United States Patent [19]

Ahrens et al.

[11] 4,042,706
[45] Aug. 16, 1977

[54] NOVEL ANTI-INFLAMMATORY PYRAZOLE DERIVATIVES AND PREPARATION THEREOF

[75] Inventors: Hanns Ahrens; Henning Koch; Eberhard Schröder; Helmut Biere; Joachim-Friedrich Kapp, all of Berlin, Germany

[73] Assignee: Schering Aktiengesellschaft, Berlin & Bergkamen, Germany

[21] Appl. No.: 712,659

[22] Filed: Aug. 9, 1976

[30] Foreign Application Priority Data

Aug. 8, 1975 Germany ............................ 2536003

[51] Int. Cl.² .................... A61K 31/415; C07D 231/12
[52] U.S. Cl. ................................. 424/273 P; 548/378
[58] Field of Search ...................... 260/310 R; 424/273

[56] References Cited

U.S. PATENT DOCUMENTS

| 3,704,241 | 11/1972 | Noguchi et al. | 424/273 |
| 3,899,508 | 8/1975 | Wikel | 260/310 R |
| 3,903,106 | 9/1975 | Katner | 260/310 R |
| 3,953,467 | 4/1976 | Fujimu et al. | 424/273 |
| 3,962,453 | 6/1976 | Ahrens et al. | 424/273 |
| 3,984,431 | 10/1976 | Gueremy et al. | 260/310 R |
| B 566,464 | 2/1976 | Hoffmann et al. | 424/273 |

FOREIGN PATENT DOCUMENTS

| 2,133,503 | 1/1972 | France |
| 2,056,173 | 5/1971 | Germany |
| 45-28987 | 9/1970 | Japan |

Primary Examiner—Donald B. Moyer
Attorney, Agent, or Firm—Millen & White

[57] ABSTRACT

Pyrazole compounds of the formula

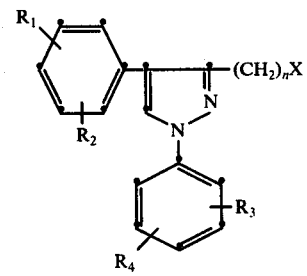

wherein $n$ is 1, 2, 3, or 4; $R_1$, $R_2$, $R_3$, and $R_4$, which can be in the ortho, meta or para position, each are hydrogen, halogen, alkyl, alkoxy, trifluoromethyl, nitro or amino; X is cyano, aminocarbonyl, lower alkoxycarbonyl, carboxy and physiologically acceptable salts thereof, have anti-inflammatory activity.

22 Claims, No Drawings

NOVEL ANTI-INFLAMMATORY PYRAZOLE DERIVATIVES AND PREPARATION THEREOF

BACKGROUND OF THE INVENTION

This invention relates to novel anti-inflammatory pyrazole compounds.

SUMMARY OF THE INVENTION

In a compositional aspect, this invention relates to novel pyrazole compounds of Formula I

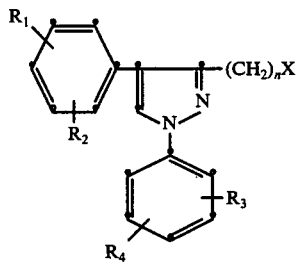

wherein
$n$ is 1, 2, 3, or 4;
$R_1$, $R_2$, $R_3$, and $R_4$ each are hydrogen, halogen, alkyl of up to 6 carbon atoms, alkoxy of up to 6 carbon atoms, trifluoromethyl, nitro or amino; and
X is cyano, carbamoyl, carbalkoxy of up to 6 carbon atoms in the alkoxy or carboxy and, when X is carboxy, physiologically acceptable salts thereof.

In another compositional aspect, this invention relates to an anti-inflammatory pharmaceutical composition, comprising a compound of Formula I, in admixture with a pharmaceutically acceptable carrier.

In a method-of-use aspect, this invention relates to a method of relieving an inflammatory condition, comprising administering to a patient afflicted therewith an anti-inflammatorily effective daily dosage of a compound of Formula I, in admixture with a pharmaceutically acceptable carrier.

In another compositional aspect, this invention relates to novel pyrazole compounds of Formula II

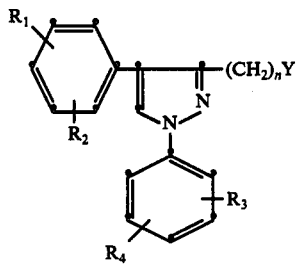

wherein $R_1$, $R_2$, $R_3$ and $R_4$ are as above; $n$ is 0, 1, 2, 3 or 4 and Y is a halogen.

In a preparative aspect, this invention relates to a process for the preparation of the pyrazole compounds of Formula I by
a. reacting a pyrazole compound of Formula II (a)

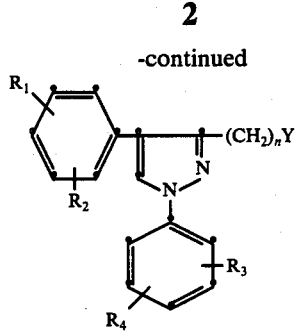

wherein $R_1$, $R_2$, $R_3$ and $R_4$ and $n$ are as above; and Y is halogen, with an alkali metal cyanide and optionally saponifying a thus-obtained nitrile; reducing any nitro groups present; and converting a thus-formed carboxylic acid to a salt thereof or esterifying the carboxylic acid with a lower alkanol; or
b. reacting a pyrazole compound of Formula II (b)

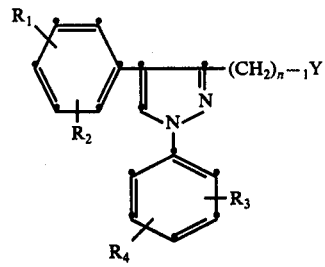

wherein $R_1$, $R_2$, $R_3$, $R_4$ and $n$ are as above; and Y is halogen, in the presence of a deprotonating agent, with a malonic acid dialkyl ester or a cyanoacetic acid alkyl ester; saponifying and decarboxylating a thus-obtained reaction product; if desired, reducing an nitro groups present; and converting a thus-formed carboxylic acid to a salt thereof or esterifying the carboxylic acid with a lower alkanol; or
c. reacting a pyrazole compound of Formula II (a)

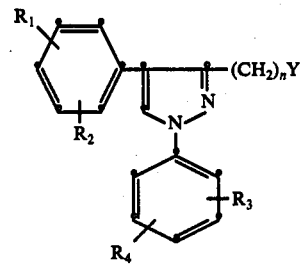

wherein $R_1$, $R_2$, $R_3$, $R_4$, $n$, and Y are as above, optionally in the presence of an ether, with magnesium or lithium; treating a thus-obtained organometallic compound with carbon dioxide; if desired, reducing any nitro groups present; and converting a thus-formed carboxylic acid to a salt, amide, nitrile or ester thereof; or
d. reacting a pyrazole compound of Formula III -continued

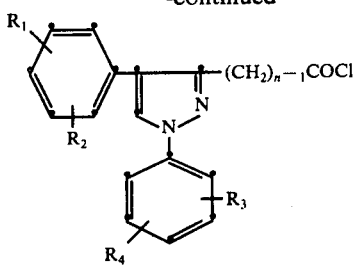

wherein $R_1$, $R_2$, $R_3$ and $R_4$ are as above, and $n$ is 1, 2, 3 or 4, with diazomethane; rearranging a thus-formed diazoketone in the presence of water, ammonia, or a lower alcohol; reducing any nitro groups present, saponifying ester groups, or dehydrating amide groups.

DETAILED DESCRIPTION

Alkoxycarbonyl or carbalkoxy means an ester in which the alkoxy has 1–6 carbon atoms, such as, for example, methoxy, ethoxy, propoxy, isopropoxy, butoxy, tert.-butoxy, pentoxy, or hexoxy, that is, carbomethoxy, carbethoxy, etc.

Physiologically acceptable salts, when X is carboxy, include, for example, alkali or alkaline earth metal salts, e.g., sodium, lithium, calcium or magnesium salts; copper salts and amine salts, e.g., N-methylglucamine, N,N-dimethylglucamine, ethanolamine, diethanolamine, and morpholine salts.

$R_1$, $R_2$, $R_3$, and $R_4$ alkyl groups of up to 6 carbon atoms, but preferably are of 1–4 carbon atoms, e.g., ethyl, propyl, isopropyl, butyl, tert.-butyl. Methyl is particularly preferred.

Compounds of Formula I include those wherein:
a. X is cyano;
b. X is carbamoyl;
c. X is carbalkoxy of up to 6 carbon atoms in the alkoxy;
d. X is carboxyl or a physiologically acceptable salt thereof;
e. $n$ is 1, including each of (a)–(d);
f. $n$ is 2, 3 or 4, including each of (a)–(d);
g. $R_1$ and $R_2$ are H, including each of (a)–(f);
h. $R_1$ or $R_2$ is halogen or trifluoromethyl, including each of (a)–(f);
i. $R_1$ or $R_2$ is alkyl, including each of (a)–(f);
j. $R_1$ or $R_2$ is alkoxy, including each of (a)–(f);
k. $R_1$ or $R_2$ is nitro, including each of (a)–(f);
l. $R_1$ or $R_2$ is amino, including each of (a)–(f);
m. $R_3$ and $R_4$ are H, including each of (a)–(l);
n. $R_3$ or $R_4$ is halogen or trifluoromethyl, including each of (a)–(l);
o. $R_3$ and $R_4$ each are halogen, including each of (a)–(l);
p. $R_3$ or $R_4$ is alkyl, including each of (a)–(l);
q. $R_3$ or $R_4$ is alkoxy, including each of (a)–(l);
r. $R_3$ or $R_4$ is nitro, including each of (a)–(l); and
s. $R_3$ or $R_4$ is amino, including each of (a)–(l).

$R_1$, $R_2$, $R_3$, and $R_4$ alkoxy groups are of up to carbon atoms, preferably 1–4 carbon atoms. Examples of preferred alkoxy are methoxy, ethoxy, propoxy and butoxy, most preferably methoxy.

$R_1$, $R_2$, $R_3$ and $R_4$ halogens are preferably fluorine or chlorine, but can be bromine or iodine.

The process of this invention by variation (a) can be conducted under conditions customarily employed for replacement of a halogen atom by a cyano group.

Compounds preferably utilized as starting materials are those of Formula II in which Y is chlorine, bromine, or iodine and $n$ is 1, 2, 3 or 4.

This reaction is preferably carried out in a dipolar aprotic solvents, e.g., dimethylformamide, N-methylacetamide, N-methylpyrrolidone, acetonitrile, dimethyl sulfoxide, or hexamethylphosphoric triamide. Sodium potassium cyanide is preferably employed as the alkali metal cyanide.

The reaction rate during this reaction can be significantly accelerated by conducting the procedure in the presence of a crown ether, as those disclosed in J. Amer. Chem. Soc, 92 (1970), 386 and 391.

The process of this invention by modification (b) is conventionally conducted by reacting a cyanoacetic acid ester, e.g., methyl or ethyl ester of cyanoacetic acid, or a malonic acid dialkyl ester, e.g., dimethyl or diethyl ester of malonic acid, in an inert solvent with a deprotonating agent to form a salt thereof, which is treated with a pyrazole derivative of Formula II (b), preferably wherein Y is a chlorine, bromine, or iodine.

Suitable inert solvents for this reaction include, for example, hydrocarbons, such as benzene, xylene, or toluene; or ethers, such as dioxane, tetrahydrofuran, or glycol dimethyl ether.

Alkali metal alcoholates, such as sodium methylate or potassium tert.-butylate; alkali metal hydrides, such as sodium or potassium hydride; alkali metal amides, such as sodium or potassium amide; or alkyl thallium compounds, such as thallium ethylate are exemplary of deprotonating agents.

The ester formed by the reaction is saponified conventionally, for example, by reaction with a base, such as sodium hydroxide, sodium carbonate, potassium hydroxide, potassium carbonate, or potassium bicarbonate, in the presence of water and is decarboxylated by heating. The decarboxylation can be conducted without a solvent or in a high-boiling solvent, such as xylene, chlorobenzene, or decahydronaphthalene.

The process of this invention by variation (c) can be accomplished conventionally by reacting, for example, a compound of Formula II (a), preferably Y is chlorine, bromine, and iodine, in a suitable solvent, such as diethyl ether, diisopropyl ether, dibutyl ether, tetrahydrofuran, or optionally benzene, with magnesium or lithium and treating a thus-formed organometallic compound with solid carbon dioxide.

The process of this invention by modification (d) is done under conditions usually employed in Arndt-Eistert syntheses. Thus, a compound of Formula III, prepared by reacting a corresponding carboxylic acid with a chlorinating agent, such as thionyl chloride, phosphorus oxychloride, or phosphorus pentachloride, is reacted with ethereal diazomethane solution and a thus-formed diazoketone can be reacted with water, a lower alcohol, or ammonia solution in the presence of colloidal copper, silver, or in the presence of silver oxide or silver nitrate, to obtain an acid, amide, or ester of Formula I.

The optionally subsequent hydrolysis of a cyano compound of Formula I likewise takes place under conditions well-known to those skilled in the art. Thus, a nitrile can be hydrolyzed, for example, with a strong mineral acid, such as hydrochloric or sulfuric acid, to a corresponding amide or, under more vigorous conditions, to a corresponding carboxylic acid.

The optional conversion of a carboxylic acid to a corresponding amide or nitrile takes place likewise using well-known procedures.

Thus, it is possible, for example, to convert an acid chloride, a mixed anhydride, or an ester corresponding to a carboxylic acid, under conventional conditions, to a corresponding amide by treatment with ammonia.

The conversion to a nitrile, an optional conversion, takes place, for example, by treating a corresponding aminocarbonyl or carbamoyl compound, under known conditions, with a dehydrating agent, such as, for example, dicyclohexyl carbodimide, carbonyl diimidazole, polyphosphoric acid, thionyl chloride, or phosphorous oxychloride.

The optional esterification of a free acid likewise takes place by known methods. Thus, an acid can be reacted, for example, with diazomethane or diazoethane, to obtain a corresponding methyl or ethyl ester. A generally applicable method is the reaction of an acid with an alcohol in the presence of carbonyl diimidazole or dicyclohexyl carbodiimide.

Furthermore, it is possible for example to react an acid in the presence of copper(I) oxide or silver oxide with an alkyl halide.

A further method of converting a free acid to a corresponding acid alkyl ester is via a corresponding dimethylformamide alkyl acetal. Furthermore, an acid can be reacted with an alcohol or a lower alkanecarboxylic acid ester of another alcohol in the presence of a strongly acidic catalyst, e.g., hydrogen chloride, sulfuric acid, perchloric acid, trifluoromethylsulfonic acid, or p-toluenesulfonic acid.

It is also possible to convert a carboxylic acid to an acid chloride, or mixed acid anhydride and to react the latter in the presence of a basic catalyst, such as pyridine, collidine, lutidine, or 4-dimethylaminopyridine, with an alcohol.

A physiologically acceptable salt of a carboxylic acid is produced, for example, by saponification of an ester with a basic catalyst or by neutralization of an acid with a physiologically acceptable base.

The following pyrazole compounds of Formula I can be produced, for example, by the process of this invention;

(1,4-diphenyl-3-pyrazolyl)-acetic acid;
3-(1,4-diphenyl-3-pyrazolyl)-propionic acid;
4-(1,4-diphenyl-3-pyrazolyl)-butyric acid;
5-(1,4-diphenyl-3-pyrazolyl)-valeric acid;
[4-phenyl-1-(4-tolyl)-3-pyrazolyl]acetic acid;
[4-phenyl-1-(2-tolyl)-3-pyrazolyl]acetic acid;
[4-phenyl-1-(2-chlorophenyl)-3-pyrazolyl]acetic acid;
[4-phenyl-1(4-chlorophenyl)-3-pyrazolyl]-acetic acid;
[4-phenyl-1-(3,4-dichlorophenyl)-3-pyrazolyl]-acetic acid;
[4-phenyl-1-(4-fluorophenyl)-3-pyrazolyl]acetic acid;
[4-phenyl-1-(2-fluorophenyl)-3-pyrazolyl]acetic acid;
[4-phenyl-1-(3-fluorophenyl)-3-pyrazolyl]acetic acid;
[4-phenyl-1-(3trifluoromethylphenyl)-3-pyrazolyl]acetic acid;
[4-(4-chlorophenyl)-1-phenyl-3-pyrazolyl]acetic acid;
[4-(4-methoxyphenyl)-1-phenyl-3-pyrazolyl]acetic acid;
[4-(4-nitrophenyl)-1-phenyl-3-pyrazolyl]-acetic acid;
[4-(4-aminophenyl)-1-phenyl-3-pyrazolyl]-acetic acid;
84-phenyl-1-(3-chloro-4-fluorophenyl)-3-pyrazolyl]acetic acid;
[4-phenyl-1-(4-trifluoromethylphenyl)-3-pyrazolyl]acetic acid;
4-(3-methoxyphenyl)-1-phenyl-3-pyrazolyl]acetic acid;
4-(4-chlorophenyl)-1-(4-fluorophenyl)-3-pyrazolyl]acetic acid;
[4-(4-methoxyphenyl)-1-(4-fluorophenyl)-3-pyrazolyl]acetic acid;

and the amides, nitriles, sodium salts, methyl esters, ethyl esters, propyl esters, butyl esters and amyl esters thereof.

The novel pyrazole compounds of Formula I are pharmacologically active and have pronounced anti-inflammatory activity, good gastric compatibility, and relatively minor toxicity. The compounds frequently have rapid onset of activity, high intensity of effectiveness, and long duration of activity. They exhibit favorable resorbability and, in galenic preparations, relatively high stability.

Pyrazole compounds of Formula I are metabolized in the body in a way different from that of the conventional compounds with anti-inflammatory activity.

The novel compounds of Formula I are suitable, in combination with the carriers used in galenic pharmacy, for example, for the treatment of a. contact dermatitis, eczemas of a great variety of types, neurodermitis, erythrodermia, first degree burns, pruritus vulvae et ani, rosacea, erythematodes cutaneus, psoriasis, lichen ruber planus et verrucosus, when applied locally;

b. acute and chronic polyarthritis, neutodermitis, bronchial asthma, hay fever, etc., when administered orally.

The drug preparations of this invention are produced in the usual way by formulating the active agents and suitable additives, carrier substances or conventional excipients into the desired forms of administration, such as tablets, dragees, capsules, solutions, ointments, inhalants, etc.

Conventional excipients, used in preparing pharmaceutical compositions of this invention are pharmaceutically a acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For enteral application, particularly suitable are tablets, dragees, or capsules. A syrup, elixir or the like can be used wherein a sweetened vehicle is employed. Sustained release compositions can be formulated including those wherein the active compound is protected with differentially degradable coatings, e.g., by microencapsulation, miltiple coatings, etc.

For topical application, these are employed as non-sprayable forms, viscous to semi-solid or solid forms comprising a carrier indigenous to topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers, or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

Especially suitable for oral application are tablets, dragees, and capsules containing, for example, 1-250 mg. of active ingredient and 50 mg. - 2g. of a pharmacologically inert carrier, such as, for example, lactose, cornstarch, potato starch, amylose, talc, gelatin, magnesium stearate, and similar materials, as well as customary additives. Suitable for topical application are powders, ointments, aerosols, and similar preparations, containing preferably 0.01-2% of the active ingredient.

The compounds of this invention are generally administered to animals, including but not limited to mammals, e.g., humans. An anti-inflammatorily effective daily dosage of the active compounds as administered orally to hunman patients generally comprises about 0.05 to 20, preferably 0.2 to 5 mg./kg. of body weight. The dose can be administered singly or as divided dosages throughout the day.

Oral or topical administration is preferred, the compounds of this invention being particularly valuable in the treatment of humans afflicted with an inflammatory condition. In this regard, they can be employed in substantially the same manner as the known compound.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

The heretofore unknown starting compounds of Formula II can be prepared from a corresponding carboxylic acid ester by reduction, for example, with lithium aluminum hydride to a carbinol and replacement of the hydroxy group of the latter by halogen, as described hereinbelow, using as an example the synthesis of 3-bromomethyl-1,4-diphenylpyrazole:

a. At room temperature, 3 g. of triethylamine and a solution of 6.78 g. of the ethyl ester of (2-chloro-2-phenylhydrazono)-acetic acid in 20 ml. of dry, ethanol-free chloroform are added in succession to 5.67 g. of α-morpholinostyrene in 35 ml. of dry, ethanol-free chloroform. The reaction mixture is stirred for 1 hour at 40° C. and for 16 hours at room temperature, washed with dilute hydrochloric acid, dilute sodium carbonate solution, and water, dried, and concentrated under vacuum.

The residue is digested with hexane and recrystallized from ethanol-hexane, thus obtaining 7.3 g. of the ethyl ester of 4-morpholino-3-phenyl-2-phenylhydrazono-3-butenoic acid, m.p. 130°-131° C.

b. 33 g. of the ethyl ester of 4-morpholino-3-phenyl-2-phenylhydrazono-3-butenoic acid is combined with 330 ml. of dioxane and 100 ml. of 2N hydrochloric acid and refluxed for 45 minutes. The reaction mixture is then concentrated under vacuum, the residue dissolved in chloroform, the chloroform solution washed, dried, and concentrated under vacuum. The remainder is recrystallized from ethanol-hexane, thus producing 21.15 g. of the ethyl ester of 1,4-diphenylpyrazole-3-carboxylic acid, m.p. 103°-104° C.

c. 4.63 g. of lithium aluminum hydride in 100 ml. of absolute tetrahydrofuran is combined under nitrogen at 0° C. dropwise with a solution of 17.2 g. of the ethyl ester of 1,4-diphenylpyrazole-3-carboxylic acid in 80 ml. of absolute tetrahydrofuran.

The reaction mixture is stirred for 30 minutes, then combined with 40 ml. of saturated aqueous sodium chloride solution, acidified with dilute hydrochloric acid, and extracted with ether. The organic phase is concentrated, digested with hexane, and the yield is 14.65 g. of 3-hydroxymethyl-1,4-diphenylpyrazole crude product, m.p. 104°-105° C.

d. 13.2 g. of the crude 3-hydroxymethyl-1,4-diphenylpyrazole is combined with 130 ml. of 63% hydrobromic acid and heated for 4 hours to 90° C.

The reaction mixture is then concentrated under vacuum, and the excess hydrogen bromide is removed by taking up the residue repeatedly with toluene and concentration under vacuum.

The residue is recrystallized from isopropanol, thus obtaining 10.8 g. of 3-bromomethyl-1,4-diphenylpyrazole, m.p. 99° C.

The following examples will serve to explain the process of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. 2.81 g. of 3-bromomethyl-1,4-diphenylpyrazole is agitated for 10 hours at 40° C. in 30 ml. of absolute acetonitril with 1.17 g. of potassium cyanide and 300 mg. of dibenzo-18-crown-6.

The reaction mixture is then concentrated under vacuum, combined with water and extracted with methylene chloride. The organic phase is washed, dried, and concentrated under vacuum.

Yield: 2.6 g. of crude (1,4-diphenyl-3-pyrazolyl)-acetonitrile.

b. 2.6 g. of crude (1,4-diphenyl-3-pyrazolyl)-acetonitrile is stirred for one hour at a reaction temperature of 50° C. with 20 ml. of concentrated hydrochloric acid. The reaction mixture is then diluted with water and extracted with methyl isobutyl ketone. The organic phase is washed, and the latter concentrated under vacuum, thus obtaining 2.3 g. of (1,4-diphenyl-3-pyrazolyl)-acetamide as a crude product.

c. 2.3 g. of crude (1,4-diphenyl-3-pyrazolyl)-acetamide is refluxed for 30 minutes with 40 ml. of 10% aqueous sodium hydroxide solution under argon.

The reaction mixture is then cooled in an ice bath, acidified with 2N hydrochloric acid, extracted with methylene chloride, and the methylene chloride phase is washed, dried, and concentrated under vacuum.

The thus-formed crude product is recrystallized from toluene, thus obtaining 1.25 g. of (1,4-diphenyl-3-pyrazolyl)-acetic acid, m.p. 131°-133° C.

EXAMPLE 2 a. A mixture of 2.6 g. of crude (1,4-diphenyl-3-pyrazolyl)-acetonitrile, prepared according to Example 1(a), and 15 ml. of 80% sulfuric acid is heated to 120° C. and agitated for 2 hours at this temperature. The reaction mixture is then poured into ice water, extracted with methylene chloride, the methylene chloride phase is washed, dried, and concentrated under vacuum.

The residue is dissolved in 5% aqueous sodium carbonate solution, precipitated with 10% hydrochloric acid, filtered off, washed, and dried at 60° C. under vacuum. The residue is recrystallized from toluene, thus obtaining 1.6 g. of (1,4-diphenyl-3-pyrazolyl)-acetic acid, m.p. 131°–133° C.

b. 200 mg. of (1,4-diphenyl-3-pyrazolyl)-acetic acid is dissolved in 10 ml. of absolute ethanol, the solution is combined with 7.6 ml. of 0.1N aqueous sodium hydroxide solution, and concentrated under vacuum.

The residue is once again taken up in 10 ml. of absolute ethanol and once again concentrated under vacuum.

The thus-obtained crude product is dissolved in a small amount of absolute ethanol, and the solution is combined with absolute diethyl ether, thus obtaining the sodium (1,4-diphenyl-3-pyrazolyl)-acetate as an amorphous powder.

EXAMPLE 3 a. A solution of 5.6 g. of thallium ethylate in 120 ml. of absolute benzene is combined, in succession, with 3.84 g. of malonic acid diethyl ester and 4.7 g. of 3-bromomethyl-1,4-diphenylpyrazole, and the mixture is agitated for 16 hours at room temperature. The reaction mixture is then diluted with diethyl ether and combined with 100 ml. of ice water. The organic phase is separated, washed, dried, and concentrated under vacuum, thus obtaining 5.3 g. of the diethyl ester of 2-(1,4-diphenyl-3-pyrazolylmethyl)-malonic acid as a crude product.

b. 6.9 g. of the thus-obtained crude diethyl ester of 2-(1,4-diphenyl-3-pyrazolylmethyl)-malonic acid is combined with 2.7 g. of sodium hydroxide, dissolved in 30 ml. of water, and 30 ml. of dioxane, and refluxed for 3 hours.

The reaction mixture is then extensively concentrated under vacuum. The residue is diluted with 100 ml. of water, and extracted with diethyl ether. The aqueous phase is acidified with concentrated hydrochloric acid to pH 1, and the thus-separated oily crude product is isolated.

The thus-formed crude product is dissolved in diethyl ether, washed with water, dried, and concentrated under vacuum, thus obtaining 4.25 g. of 2-(1,4-diphenyl-3-pyrazolylmethyl)-malonic acid, m.p. 172° C.

c. 4.1 g. of 2-(1,4-diphenyl-3-pyrazolylmethyl)-malonic acid is gradually heated to 200° C. The reaction temperature is maintained for 20 minutes at 200° C., then allowed to cool down, and the thus-obtained product is recrystallized from toluene. Yield: 2.9 g. of 3-(1,4-diphenyl-3-pyrazolyl)-propionic acid, m.p. 128°–129° C.

d. 200 mg. of 3-(1,4-diphenyl-3-pyrazolyl)-propionic acid is converted, under the conditions of Example 2(b), into the amorphous sodium 3-(1,4-diphenyl-3-pyrazolyl)-propionate.

EXAMPLE 4 a. 2.7 g. of 3-(1,4-diphenyl-3-pyrazolyl)-propionic acid is combined with 10 ml. of thionyl chloride distilled over linseed oil. The mixture is refluxed for 2 hours and then concentrated under vacuum. The remainder is combined with 25 ml. of absolute benzene, again concentrated under vacuum, and the yield is 2.6 g. of 3-(1,4-diphenyl-3-pyrazolyl)-propionyl chloride is a crude product.

b. 50 mg. of crude 3-(1,4-diphenyl-3-pyrazolyl)-propionyl chloride is mixed with 5 ml. of absolute benzene and 5 ml. of absolute ethanol. The mixture is then combined dropwise with 0.2 ml. of pyridine, and the mixture is allowed to stand for 16 hours at room temperature. The mixture is then diluted with 20 ml. of benzene, thereafter washed with water, dilute hydrochloric acid, and water, dried, and concentrated under vacuum. The residue is recrystallized from acetonehexane, thus obtaining 38 mg. of the ethyl ester of 3-(1,4-diphenyl-3-pyrazolyl)-propionic acid, m.p. 94.5°–98.5° C.

EXAMPLE 5 a. 1.9 g. of crude 3-(1,4-diphenyl-3-pyrazolyl)-propionyl chloride in 20 ml. of absolute ether is combined with an ethereal solution of diazomethane solution — prepared from 3.5 g. of nitrosomethylurea, 50 ml. of anhydrous ether, and 11 ml. of 50% aqueous potassium hydroxide solution — and allowed to stand for 4 hours at room temperature.

The reaction mixture is then concentrated under vacuum, combined with 40 ml. of ethanol, heated to 60° C., combined with 0.2 g. of freshly prepared silver oxide, and heated until the evolution of nitrogen is terminated.

The reaction mixture is then clarified with active carbon, filtered, concentrated under vacuum, and the yield is 1.7 g. of the ethyl ester of 4-(1,4-diphenyl-3-pyrazolyl)-butyric acid as a crude product.

b. 1.7 g. of the ethyl ester of 4-(1,4-diphenyl-3-pyrazolyl)-butyric acid is dissolved in 20 ml. of ethanol, combined with 5 ml. of 10% sodium hydroxide solution, and refluxed for 2 hours. The ethanol is then removed under vacuum, the mixture diluted with 10 ml. of water, acidified with hydrochloric acid to pH 1, and the thus-separated product is filtered off.

The thus-obtained crude produce is washed with water, dried under vacuum at 60° C., and recrystallized from toluene, thus producing 1.05 g. of 4-(1,4-diphenyl-3-pyrazolyl)-butyric acid, m.p. 107°–109° C.

EXAMPLE 6 a. A solution of 15.2 g. of sodium nitrite in 40 ml. of water is added dropwise to a solution at 0° C. of 21.4 g. of p-toluidine and 400 ml. of 7.5% hydrochloric acid. The suspension of p-toluene diazonium chloride obtained is added dropwise at 5° C. to a mixture consisting of 36.2 g. of 2-chloroacetic acid ethyl ester, 400 ml. of 50% ethanol and 164 g. of sodium acetate. The mixture then is stirred for three hours at 20° C. and extracted with ethyl acetate. The organic phase is concentrated and the residue is treated with petroleum ether. 41 g. of 2-chloro-2-(4-methyl-phenylhydrazono)-acetic acid ethyl ester with a melting point of 100°–101° C., is obtained.

b. A solution of 24.7 g. of 2-chloro-2-(4-methyl-phenyhydrazono)-acetic acid ethyl ester in 100 ml. of chloroform is added dropwise to a solution of 18.9 g. of α-morpholinostyrene in 100 ml. of chloroform and 13.8 g. of triethylamine. The reaction mixture is allowed to stand for 1 hour at 50° C. and for 16 hours at 20° C., whereupon it is washed with 2N hydrochloric acid and then with a saturated solution of sodium bicarbonate. The chloroform solution then is concentrated in vacuum and the residue is treated with petroleum ether. One obtains 27.6 g. of 2-(4-methylphenylhydrazono)-3-morpholinomethylene-3-phenypropionic acid ethyl ester with a melting point of 131°-132° C.

c. 27.6 g. of 2-(4-methylphenylhydrazono)-3-morpholinomethylene-3-phenylpropionic acid ethyl ester are treated with 260 ml. of dioxane and 80 ml. of 2N hydrochloric acid and are heated under reflux for 45 minutes. The reaction is allowed to cool and then is concentrated in vacuum, the residue being taken up in chloroform. The chloroform phase is washed with water and concentrated in vacuum. The residue is treated with petroleum ether. 17.1 g. of 4-phenyl-1-(4-tolyl)-3-pyrazolecarboxylic acid ethyl ester, melting point 115°-117° C., is obtained.

d. A solution consisting of 16.8 g. of 4-phenyl-1-(4-tolyl)-3-pyrazolecarboxylic acid ethyl ester in 100 ml. of tetrahydrofuran is added dropwise to a suspension cooled to 0° C., of 4.3 g. of lithium aluminum hydride in 100 ml. of tetrahydrofuran. The mixture is stirred for 1 hour and then treated with 25 ml. of saturated sodium chloride solution and then with 63 ml. of 20% hydrochloric acid. The reaction mixture then is extracted with ether. The ether phase is concentrated in vacuum and the residue is treated with petroleum ether to obtain 12 g. of [4-phenyl-2-(4-phenyl-1-(4-tolyl)-3-pyrazolyl]-methanol with a melting point of 125° C.

e. 2.65 g. of [4-phenyl-1-(4-tolyl)-3-pyrazolyl]-methanol are heated in 60 ml. of 63% hydrobromic acid for 5 hours at 90° C. The reaction mixture then is diluted with water. The precipitated product is filtered under vacuum and recrystallized from isopropanol to obtain 2.9 g. of 3-bromomethyl-4-phenyl-1-(4-tolyl)-pyrazole with a melting point of 98° C.

f. 5.9 g. of 3-bromomethyl-4-phenyl-1-(4-tolyl)-pyrazole are reacted with 4.7 g. of potassium cyanide in 70 ml. of acetonitrile and 500 mg. of dibenzo-18-crown-6 and are stirred for 10 hours at 40° C. The reaction mixture then is concentrated under vacuum. The residue is taken up in water and then is extracted with methylene chloride; the methylene chloride phase is washed and concentrated. The residue is recrystallized from methanol to obtain 4.7 g. of [4-phenyl-1-(4-tolyl)-3-pyrazolyl]acetonitrile with a melting point of 91°-92° C.

g. 4.7 g. of [4-phenyl-1-(4-tolyl)-3-pyrazolyl]acetonitrile are heated for 2 hours at 120° C. in 27 ml. of 80% sulfuric acid. The reaction mixture is allowed to cool, then is diluted with water and extracted with methylene chloride. The organic phase is washed and concentrated. The residue is recrystallized from toluene. One obtains 3.2 g. of [4-phenyl-1-(4-tolyl)-3-pyrazolyl]-acetic acid with a melting points of 124°-125° C.

EXAMPLE 7 a. 2.5 g. of [4-phenyl-1-(4-tolyl)-3-pyrazolyl]acetonitrile are stirred together with 20 ml. of concentrated hydrochloric acid for one hour at a reaction temperature of 50° C. The reaction mixture then is diluted with water and extracted with methyl isobutyl ketone. The organic phase is washed and concentrated in vacuum to obtain 1.9 g. of [4-phenyl-1-(4-tolyl)-3-pyrazolyl]-acetamide as a crude material b. 1.9 g. of [4-phenyl-1-(4-tolyl)-3-pyrazolyl]acetamide crude product are heated under reflux in 40 ml. of 10% aqueous sodium hydroxide under an atmosphere of argon for 30 minutes. The reaction mixture then is cooled in the ice bath, acidified with 2N hydrochloric acid and extracted with methylene chloride. The methylene chloride extract then is washed and dried and concentrated in vacuum. The crude product so obtained is recrystallized from toluene. One obtains 0.95 mg. (milligrams) of [4-phenyl-1-(4-tolyl)-3-pyrazolyl]acetic acid with a melting point of 124.5°-126° C.

EXAMPLE 8 a. 2.5 g. of [4-phenyl-1-(4-tolyl)-3-pyrazolyl]acetic acid are reacted with 10 ml. of thionyl chloride distilled over linseed oil and the mixture is heated under reflux for two hours. The reaction mixture then is concentrated in vacuum. The residue is treated with 25 ml. of absolute benzene and again concentrated in vacuum. One obtains 2.2 g. of [4-phenyl-1-(4-tolyl)-3-pyrazolyl]-acetyl chloride as crude material.

b. 2.2 g. of [4-phenyl-1-(4-tolyl)-3-pyrazolyl]acetyl chloride crude product are reacted with 5 ml. of absolute benzene and 5 ml. of absolute ethanol. 0.2 ml. of pyridine are added dropwise to this mixture, which is allowed to stand at room temperature for 16 hours, and then diluted with 20 ml. of benzene. The reaction mixture then is washed in turn with water, diluted hydrochloric acid and water; dried and concentrated in vacuum. The residue is recrystallized from acetone/hexane. 1.7 g. of [4-phenyl-1-(4-tolyl)-3-pyrazolyl]-acetic acid ethyl ester with a melting point of 76°-79° C., is obtained.

EXAMPLE 9 a. Under the conditions of Example 6(a), o-toluidine is converted into 2-chloro-2-(2-methylphenylhydrazone)-acetic acid ethyl ester with a melting point of 72° C.

b. The product so obtained is converted to 2-(2-methylphenylhydrazono)-3-morpholinomethylene-3-phenylpropionic acid ethyl ester with a melting point of 109° C. as described in Example 6(b).

c. Following the conditions of Example 6(c), the compound obtained is converted into 4-phenyl-1-(2-tolyl)-3-pyrazolecarboxylic acid ethyl ester with a melting point of 80° C.

d. The product obtained is reduced as described in Example 6(d) to [4-phenyl-1-(2-tolyl)-3-pyrazolyl]methanol, melting point, 121° C.

e. Bromination of this compound as in Example 6(e) yields 3-bromomethyl-4-phenyl-1-(2-tolyl)-pyrazole with a melting point of 67° C.

f. Under the conditions of Example 6(f), the bromide is converted to [4-phenyl-1-(2-tolyl)-3-pyrazolyl]acetonitrile with a melting point of 23° C.

g. The nitrile so obtained is saponified as in Example 6(g). One obtains [4-phenyl-1-(2-tolyl)-3-pyrazolyl]acetic acid with a melting point of 177° C.

EXAMPLE 10 a. Under conditions of Example 6(a), o-chloroaniline is converted to 2-chloro-2-(2-chlorophenylhydrazono)-acetic acid ethyl ester with a melting point of 92° C.

b. The compound so obtained is converted as described in Example 6(b) into 2-(2-chlorophenylhydrazone)-3-morpholinomethylene-3-phenylpropionic acid ethyl ester with a melting point of 122° C.

c. Using the conditions of Example 6(c), the product obtained is converted to 4-phenyl-1-(2-chlorophenyl)-3-pyrazolecarboxylic acid ethyl ester with a melting point of 109° C.

d. As described in Example 6(d), the reaction of the compound of Example 10(c) yields [4-phenyl-1-(2-chlorophenyl)-3-pyrazolyl]methanol with a melting point of 132° C.

e. Using the conditions of Example 6(e), bromination of the alcohol leads to 3-bromomethyl-4-phenyl-2-(2-chlorophenyl)-pyrazole with a melting point of 91° C.

f. By conditions of Example 6(f), the bromo compound is converted into [4-phenyl-1-(2-chlorophenyl)-3-pyrazolyl]acetonitrile with a melting point of 62° C.

g. The nitrile so obtained is converted into [4-phenyl-1-(2-chlorophenyl)-3-pyrazolyl]acetic acid with a melting point of 146° C. by the conditions of Example 6 (g).

EXAMPLE 11

Following the conditions of Examples 6(a)–6(f), [4-phenyl-1-(4-chlorophenyl)-3-pyrazolyl]acetonitrile with a melting point of 121° C. is prepared from 4-chloroaniline and saponified as described in Example 6(g) to [4-phenyl-1-(4-chlorophenyl)-3-pyrazolyl]-acetic with a melting point of 137° C.

The intermediates obtained in the preparation of the nitrile have the following physical properties:
Melting points:
2-chloro-2-(4-chlorophenylhydrazono)-acetic acid ethyl ester 150° C.
2-(4-chlorophenylhydrazono)-3-morpholinomethylene-3-phenylpropionic acid 164° C.
4-phenyl-1-(4-chlorophenyl)-3-pyrazolecarboxylic acid ethyl ester 91° C.
[4-phenyl-1-(4-chlorophenyl)-3-pyrazolyl]methanol 117° C.,
3-bromomethyl-4-phenyl-1-(4-chlorophenyl)-pyrazole 125° C.

EXAMPLE 12

Using the conditions described in Example 6(a) through 6(f), [4-phenyl-1-(3,4-dichlorophenyl)-3-pyrazolyl]acetonitrile with a melting point of 131° C. is prepared from 3,4-dichloroaniline. The product then is saponified under the conditions of Example 6(g) to [4-phenyl-1-(3,4-dichlorophenyl)-3-pyrazolyl]-acetic acid with a melting point of 158° C.

The intermediate products obtained during nitrile preparation have the following physical properties:
Melting points:
2-chloro-2-(3,4-dichlorophenylhydrazono)-acetic acid ethyl ester 154° C.
2-(3,4-dichlorophenylhydrazono)-3-morpholinomethylene-3-phenylpropionic acid 141° C.
4-phenyl-1-(3,4-dichlorophenyl)-3-pyrazolecarboxylic acid ethyl ester 117° C.
[4-phenyl-1-(3,4-dichlorophenyl)-3-pyrazolyl]methanol, 121° C.
3-bromomethyl-4-phenyl-1-(3,4-dichlorophenyl)-pyrazole 108° C.

EXAMPLE 13

Under the conditions of Example 6(a)–6(f), [4-phenyl-1-(4-fluorophenyl)-3-pyrazolyl]acetonitrile with a melting point of 79° C. is prepared from p-fluoroaniline and is saponified as described in Example 6(g) to [4-phenyl-1-(4-fluorophenyl)-3-pyrazolyl]acetic acid with a melting point of 171° C.

The intermediate products obtained in the nitrile preparation have the following physical properties:
The melting points are:
2-chloro-2-(4-fluorophenylhydrazono)-acetic acid ethyl ester 109° C.
2-(4-fluorophenylhydrazono)-3-morpholinomethylene-3-phenylpropionic acid 161° C.
4-phenyl-1-(4-fluorophenyl)-3-pyrazolecarboxylic acid ethyl ester 125° C.
[4-phenyl-1-(4-fluorophenyl)-3-pyrazolyl]methanol 146° C.,
3-bromomethyl-4-phenyl-1-(4-fluorophenyl)-pyrazole 89° C.

EXAMPLE 14

Using the conditions of Example 6(a) through 6(f), [4-phenyl-1-(2-fluorophenyl)-3-pyrazolyl]-acetonitrile with a melting point of 70° C. is prepared from o-fluoroaniline and saponified as described in Example 6(g) to [4-phenyl-1-(2-fluorophenyl)-3-pyrazolyl]-acetic acid with a melting point of 154° C.

The intermediate products obtained during nitrile preparation had the following physical properties:
The melting points are:
2-chloro-2-(2-fluorophenylhydrazono)acetic acid ethyl ester 70° C.
2-(2-fluorophenylhydrazono)-3-morpholinomethylene-3-phenylpropionic acid 99° C.
4-phenyl-1-(2-fluorophenyl)-3-pyrazolecarboxylic acid ethyl ester 62° C.
[4-phenyl-1-(2-fluorophenyl)-3-pyrazolyl]methanol 109° C.,
3-bromomethyl-4-phenyl-1-(2-fluorophenyl)-pyrazole 102° C.

EXAMPLE 15

Under conditions described in Example 6(a) through 6(f), [4-phenyl-1-(3-fluorophenyl)-3-pyrazolyl]-acetonitrile with a melting point of 74° C., was prepared from m-fluoroaniline and saponified under the conditions described in Example 6(g) to [4-phenyl-1-(3-fluorophenyl)-3-pyrazolyl]acetic acid with a melting point of 159° C.

The intermediate products obtained during nitrile preparation had the following physical properties.
The melting points are:
2-chloro-2-(3-fluorophenylhydrazono)-acetic acid ethyl ester, 111° C.
2-(3-fluorophenylhydrazono)-3-morpholinomethylene-3-phenylpropionic acid, 110° C.
4-phenyl-1-(3-fluorophenyl)-3-pyrazolecarboxylic acid ethyl ester, 81° C.
[4-phenyl-1-(3-fluorophenyl)-3-pyrazolyl]methanol, 74° C.,
3-bromomethyl-4-phenyl-1-(3-fluorophenyl)-pyrazole, 75° C.

EXAMPLE 16

Using conditions of Example 6(a) through 6(f), [4-phenyl-1-(3-trifluoromethylphenyl)-3-pyrazolyl]acetonitrile with a melting point of 76° C. was prepared from m-trifluoromethylaniline and saponified under the conditions of Example 6(g) to [4-phenyl-1-(3-trifluoromethylphenyl)-3-pyrazolyl]acetic acid with a melting point of 169° C.

The intermediate products obtained during the nitrile preparation had the following physical properties:
The melting points are:

2-chloro-2-(3-trifluoromethylphenylhydrazono)acetic acid ethyl ester, 131° C.;
2-(3-trifluoromethylphenylhydrazono)-3-morpholinomethylene-3-phenylpropionic acid, 125° C.;
4-phenyl-1-(3-trifluoromethylphenyl)-3-pyrazolecarboxylic acid ethyl ester, 66° C.;
[4-phenyl-1-(3-trifluoromethylphenyl)-3-pyrazolyl]methanol, 94° C.;
3-bromomethyl-4-phenyl-1-(3-trifluoromethyl phenyl)-pyrazole, 120° C.

EXAMPLE 17 a. Under conditions of Example 6(b), 22.7 g. of α-dimethylamino-4-nitrostyrene are reacted with 19.2 g. of 2-chloro-2-phenylhydrazonoacetic acid ethyl ester and worked up. 3-Dimethylaminomethylene-3-(4-nitrophenyl)-2-phenylhydrazonopropionic acid ethyl ester with a melting point of 139° C., is obtained.

b. The compound so obtained is cyclized under conditions given in Example 6(c) to 4-(4-nitrophenyl)-3-pyrazolecarboxylic acid ethyl ester with a melting point of 143° C.

c. 24 g. of the compound obtained in (b) are dissolved in 500 ml. of ethanol and reacted with 5 g. of Raney nickel and hydrogenated at room temperature under atmospheric pressure. The catalyst then is filtered off, the filtrate is concentrated in vacuum, and the residue is recrystallized from methanol. One obtains 20 g. of 4-(4-aminophenyl)-1-phenyl-3-pyrazolecarboxylic acid ethyl ester with a melting point of 142° C.

d. 3.1 g. of 4-(4-aminophenyl)-1-phenyl-3-pyrazolecarboxylic acid ethyl ester in 13 ml. of 15% hydrochloric acid at −5° C. are reacted with a solution of 760 mg. of sodium nitrite in 1.5 ml. of water; then 25 ml. of 3% hydrochloric acid is added to the mixture and the cold mixture (−5° C.) is added dropwise to a warm solution (60° C.) of 1.5 g. of copper (II) chloride in 30 ml. of 12% hydrochloric acid. This mixture is allowed to stand 10 minutes at 60° C. Then it is cooled and extracted with ethyl acetate. The extract is concentrated and the residue is taken up in toluene and filtered through a silica gel column. The solution then is concentrated and one obtains 2.47 g. of 4-(4-chlorophenyl)-1-phenyl-3-pyrazolecarboxylic acid ethyl ester with a melting point of 96° C.

e. Under the conditions of Example 6(d) through 6(g), 4-(4-chlorophenyl)-1-phenyl-3-pyrazolecarboxylic acid ethyl ester is converted into [4-(4-chlorophenyl)-1-phenyl-3-pyrazolyl]acetic acid with a melting point of 142° C.

The intermediate products obtained in the synthesis of this compound have the following physical properties:
The melting points are: [4-(4-chlorophenyl)-1-phenyl-3-pyrazolyl]methanol, 145° C.
3-bromoethyl-4-(4-chlorophenyl)-1-phenylpyrazole, 110° C.
[4-(4-chlorophenyl)-1-phenyl-3-pyrazolyl]acetonitrile, 97° C.

EXAMPLE 18 a. 2.4 gm. of 4-(4-aminophenyl)-1-phenyl-3-pyrazolecarboxylic acid ethyl ester are reacted with 28 ml. of 1N hydrochloric acid, cooled to 0° C. and slowly diazotized with a solution of 830 mg. of sodium nitrite in 10 ml. of water. The mixture is diluted with 10 ml. of water and stirred for 15 minutes at 0° C. Thereupon, 953 mg. of zinc chloride are added to the mixture, which is allowed to stand for 30 minutes. The separated precipitate is filtered under vacuum, dried and taken up in 50 ml. of methanol and allowed to stand at room temperature for 16 hours, and then is heated for one hour under reflux. The reaction mixture is concentrated under vacuum and the residue is dissolved in benzene. The benzene phase is washed and concentrated in vacuum. The residue is reacted with 2 equivalents of sodium hydroxide and 2.02 g. of dimethyl sulfate and heated at 80° C. for 30 minutes. After cooling, the mixture is extracted with methylene chloride, the organic phase is concentrated and the residue is recrystallized from isopropanol. 1.92 g. of 4-(4-methoxyphenyl)-1-phenyl-3-pyrazolecarboxylic acid ethyl ester with a melting point of 94° C., is obtained.

b. Under conditions of Example 6(d) through 6(g), 4-(4-methoxyphenyl)-1-phenyl-3-pyrazolecarboxylic acid ethyl ester is converted into [4-(4-methoxyphenyl)-1-phenyl-3-pyrazolyl]acetic acid with a melting point of 101° C.

The intermediate products obtained in this synthesis have the following physical properties:
The melting points are:
[4-(4-methoxyphenyl)-1-phenyl-3-pyrazolyl]methanol, 101° C.
3-chloromethyl-4-(4-methoxyphenyl)-1-phenylpyrazole, 125° C. The compound is obtained from the above compound by reaction with 1.1 equivalents of methanesulfonyl chloride in pyridine at −15° C.
[4-(4-methoxyphenyl)-1-phenyl-3-pyrazolyl]-acetonitrile, 83° C.

EXAMPLE 19 a. 2 g. of 4-(4-nitrophenyl)-1-phenyl-3-pyrazolecarboxylic acid ethyl ester are reacted with 70 ml. of isopropanol and with 15 ml. of 40% potassium hydroxide by heating for 2 hours under reflux. The reaction mixture is concentrated to a small volume under vacuum and the precipitated crystals are filtered under vacuum. One obtains 1.67 g. of 4-(4-nitrophenyl)-1-phenyl-3-pyrazolecarboxylic acid with a melting point of 273° C.

b. The carboxylic acid is reacted with 0.5 ml. of dimethylformamide and 10 ml. of thionyl chloride and heated for 14 hours under reflux. The reaction mixture is concentrated in vacuum and one obtains 1.55 g. of 4-(4-nitrophenyl)-1-phenyl-3-pyrazolecarboxylic acid chloride with a melting point of 226° C.

c. The acid chloride is reacted with 25 ml. of dioxane and 5 ml. of ether and cooled to 10° C. Three equivalents of ethereal diazomethane solution are added to the mixture which then is allowed to stand for 2 hours at 10° C. The reaction mixture is concentrated in vacuum and the residue is reacted with 80 ml. of isoamyl alcohol and filtered. A solution of 4.4 g. of silver benzoate in 45 ml. of triethylamine is added dropwise to the above obtained solution and the whole is allowed to stand for 72 hours. This is followed by filtration, washing of the filtrate with aqueous sodium carbonate solution and vacuum concentration. The residue is purified by chromatography through a silica gel column using cyclohexane-acetic ester. One obtains 395 mg. of [4-(4-nitrophenyl)-1-phenyl-3-pyrazolyl]acetic acid isoamyl ester with a melting point of 81° C.

d. The ester so obtained is saponified as in Example 19(a). One obtains 145 mg. of [4-(4-nitrophenyl)-1-phenyl-3-pyrazolyl]acetic acid with a melting point of 306° C.

EXAMPLE 20

210 mg. of [4-(4-nitrophenyl)-1-phenyl-3-pyrazolyl]acetic acid are reacted with 20 ml. of glycol monomethyl ether and 1 g. of Raney nickel and hydrogenated at room temperature under normal pressure. The reaction is worked up as described in Example 17(c). [4-(4-Aminophenyl)-1-phenyl-3-pyrazolyl]acetic acid is obtained.

EXAMPLE 21

Under conditions of Example 6(a) through 6(g), [4-phenyl-1-(3-chloro-4-fluorophenyl)-3-pyrazolyl]acetic acid is prepared from 4-trifluoromethylaniline.

EXAMPLE 22

Under conditions of Example 6(a) through 6(g), [4-phenyl-1-(4-trifluoromethylphenyl)-3-pyrazolyl]acetic acid is prepared from 4-trifluoromethylaniline.

EXAMPLE 23

3-Methoxy-α-morpholinostyrene and 2-chloro-2-phenylhydrazonoacetic acid ethyl ester are reacted to form [4-(3-methoxyphenyl)-1-phenyl-3-pyrazolyl]acetic acid as described in Example 6(b) through 6(g).

EXAMPLE 24 a. Under conditions of Example 17(a) through 17(c), α-dimethylamino-4-nitrostyrene is reacted with 2-chloro-2-(4-fluorophenylhydrazono)acetic acid. 4-(4-Aminophenyl)-1-(4-fluorophenyl)-3-pyrazolecarboxylic acid ethyl ester is obtained.

b. The compound so obtained is converted as described in Example 17(d) through 17(e) to [4-(4-chlorophenyl)-1-(4-fluorophenyl)-3-pyrazolyl]acetic acid.

EXAMPLE 25

Under conditions of Example 18(a) and 18(b), 4-(4-aminophenyl)-1-(4-fluorophenyl)-3-pyrazole-carboxylic ethyl ester is converted to [4-(4-methoxyphenyl)-1-(4-fluorophenyl)-3-pyrazolyl]acetic acid.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pyrazole compound of the formula

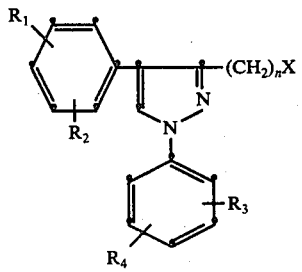

wherein
$n$ is 1, 2, 3, or 4;

$R_1$, $R_2$, $R_3$, and $R_4$ each are hydrogen, halogen, alkyl of up to 6 carbon atoms, alkoxy of up to 6 carbon atoms, trifluoromethyl, nitro or amino; and X is cyano, carbamoyl, carbalkoxy of up to 6 carbon atoms in the alkoxy or carboxy and, when X is carboxy, physiologically acceptable salts thereof.

2. A compound of claim 1, wherein X is cyano.
3. A compound of claim 1, wherein X is carbamoyl.
4. A compound of claim 1, wherein X is carbalkoxy of up to 6 carbon atoms in the alkoxy.
5. A compound of claim 1, wherein S is carboxy or a physiologically acceptable salt thereof.
6. A compound of claim 1, wherein $n$ is 1.
7. A compound of claim 1, wherein $n$ is 2, 3 or 4.
8. (1,4-Diphenyl-3-pyrazolyl)-acetonitrile, a compound of claim 1.
9. (1,4-Diphenyl-3-pyrazolyl)-acetamide, a compound of claim 1.
10. (1,4-Diphenyl-3-pyrazolyl)-acetic acid, a compound of claim 1.
11. 3-(1,4-Diphenyl-3-pyrazolyl)-propionic acid, a compound of claim 1.
12. Sodium 3-(1,4-diphenyl-3-pyrazolyl)-propionate, a compound of claim 1.
13. Ethyl ester of 3-(1,4-diphenyl-3-pyrazolyl)-propionic acid, a compound of claim 1.
14. Ethyl ester of 4-(1,4-diphenyl-3-pyrazolyl)butyric acid, a compound of claim 1.
15. 4-(1,4-Diphenyl-3-pyrazolyl)-butyric acid, a compound of claim 1.
16. [4-Phenyl-1-(4-tolyl)-3-pyrazolyl]acetonitrile,
[4-phenyl-1-(2-tolyl)-3-pyrazolyl]acetonitrile,
[4-phenyl-1-(2-chlorophenyl)-3-pyrazolyl]acetonitrile,
[4-phenyl-1-(4-chlorophenyl)-3-pyrazolyl]acetonitrile,
[4-phenyl-1-(3,4-dichlorophenyl)-3-pyrazolyl]acetonitrile,
[4-phenyl-1-(4-fluorophenyl)-3-pyrazolyl]acetonitrile,
[4-phenyl-1-(2-fluorophenyl)-3-pyrazolyl]acetonitrile,
[4-phenyl-1-(3-fluorophenyl)-3-pyrazolyl]acetonitrile,
[4-phenyl-1-(3-trifluoromethylphenyl)-3-pyrazolyl]acetonitrile,
[4-(4-chlorophenyl)-1-phenyl-3-pyrazolyl]acetonitrile, or
[4-(4-methoxyphenyl)-1-phenyl-3-pyrazolyl]acetonitrile, a compound of claim 1.
17. [4-Phenyl-1-(4-tolyl)-3-pyrazolyl]acetic acid,
[4-phenyl-1-(2-tolyl)-3-pyrazolyl]acetic acid,
[4-phenyl-1-(2-chlorophenyl)-3-pyrazolyl]acetic acid,
4-phenyl-1-(4-chlorophenyl)-3-pyrazolyl]acetic acid,
[4-phenyl-1-(3,4-dichlorophenyl)-3-pyrazolyl]acetic acid,
[4-phenyl-1-(4-fluorophenyl)-3-pyrazolyl]acetic acid,
[4-phenyl-1-(2-fluorophenyl)-3-pyrazolyl]acetic acid,
[4-phenyl-1-(3-fluorophenyl)-3-pyrazolyl]acetic acid,
[4-phenyl-1-(3-trifluoromethylphenyl)-3-pyrazolyl]acetic acid,
[4-(4-chlorophenyl)-1-phenyl-3-pyrazolyl]acetic acid,
[4-(4-methoxyphenyl)-1-phenyl-3-pyrazolyl]acetic acid,
[4-(4nitrophenyl)-1-phenyl-3-pyrazolyl]acetic acid,
[4-(4-aminophenyl)1-phenyl-3-pyrazolyl]acetic acid,
[4-phenyl-1-(3-chloro-4-fluorophenyl)-3-pyrazolyl]acetic acid,
[4-phenyl-1-(4-trifluoromethylphenyl)-3-pyrazolyl]acetic acid,

[4-(3-methoxyphenyl)-1-phenyl-3-pyrazolyl]acetic acid,

[4-(4-chlorophenyl)-1-(4-fluorophenyl)-3-pyrazolyl]acetic acid, or

[4-(4-methoxyphenyl)-1-(4-fluorophenyl)-3-pyrazolyl]acetic acid, a compound of claim 1.

18. [4-Phenyl-1-(4-tolyl)-3-pyrazolyl]acetamide, a compound of claim 1.

19. Isoamyl ester of [4-(4-nitrophenyl)-1-phenyl-3-pyrazolyl]acetic acid, a compound of claim 1.

20. Ethyl ester of [4-phenyl-1-(4-tolyl)-3-pyrazolyl]acetic acid, a compound of claim 1.

21. An anti-inflammatory pharmaceutical composition, comprising a compound of claim 1, in admixture with a pharmaceutically acceptable carrier.

22. A method of treating an inflammatory condition, comprising administering to a patient afflicted therewith an anti-inflammatorily effective daily dosage of a compound of claim 1, in admixture with a pharmaceutically acceptable carrier.

* * * * *

UNITED STATES PATENT AND TRADEMARK OFFICE
CERTIFICATE OF CORRECTION

PATENT NO. : 4,042,706
DATED : August 16, 1977
INVENTOR(S) : HANNS AHRENS ET AL.

It is certified that error appears in the above-identified patent and that said Letters Patent are hereby corrected as shown below:

Claim 5, column 18, line 11: Please delete "S" and replace it with -- X --.

Signed and Sealed this

Twenty-second Day of November 1977

[SEAL]

Attest:

RUTH C. MASON
*Attesting Officer*

LUTRELLE F. PARKER
*Acting Commissioner of Patents and Trademarks*